United States Patent [19]
Majlessi

[11] Patent Number: 5,871,454
[45] Date of Patent: Feb. 16, 1999

[54] PERCUTANEOUS EXCISIONAL BIOPSY DEVICE

[76] Inventor: Heshmat Majlessi, 233 Purchase St., Rye, N.Y. 10580

[21] Appl. No.: 841,452
[22] Filed: Apr. 22, 1997
[51] Int. Cl.⁶ .................................................. A61B 10/00
[52] U.S. Cl. ............................ 600/564; 600/565; 604/22
[58] Field of Search ................................... 600/563, 564, 600/565, 566, 567; 604/22, 29

[56] References Cited

U.S. PATENT DOCUMENTS

| 4,461,305 | 7/1984 | Cibley | 128/754 |
| 4,895,560 | 1/1990 | Papantonakos | 604/22 |
| 4,966,604 | 10/1990 | Reiss | 606/159 |
| 5,030,201 | 7/1991 | Palestrant | 604/22 |
| 5,192,291 | 3/1993 | Pannek, Jr. | 604/22 |
| 5,224,945 | 7/1993 | Pannek, Jr. | 604/22 |
| 5,318,576 | 6/1994 | Plassche, Jr. et al. | 604/22 |
| 5,376,100 | 12/1994 | Lefebvre | 604/22 |
| 5,409,013 | 4/1995 | Clement | 128/753 |
| 5,433,725 | 7/1995 | Christian et al. | 606/207 |
| 5,560,373 | 10/1996 | De Santis | 128/753 |
| 5,575,293 | 11/1996 | Miller et al. | 128/752 |

Primary Examiner—Max Hindenburg
Assistant Examiner—Charles Marmor, II

[57] ABSTRACT

An elongate outer sleeve is mounted on a support and defines an axis and distal and proximate ends in relation to said support. An elongate inner tube is generally coaxial with and contained within said outer sleeve. A drive selectively rotates the inner tube about the axis relative to the outer sleeve. The outer sleeve is mounted for selected movement along the axis relative to the inner tube between a first position in which the remote end of the inner tube in contained within and covered by the outer sleeve and a second position in which the remote end of the inner tube is exposed, the inner tube being provided at the remote end with a cutting assembly consisting of a plurality of blade elements radially spaced about the axis and biassed to urge the blade elements to expand outwardly into their normal operative cutting positions when moved exteriorly of the remote end of the outer sleeve, adjacent blade elements being collapsible for containment within the outer sleeve and forming laterally-directed opening which communicate with a channel within the inner tube. Carrier fluid is dispensed at the remote end of the outer sleeve. A receptacle is provided for collecting tissue excised by the expanded blades carried through the inner tube from the remote to the proximate ends by the carrier fluid. Also, a source of suction is provided for extracting cells and tissue excised by the blade elements and transported by the carrier fluid through the inner tube and into the means for collection.

15 Claims, 3 Drawing Sheets

PERCUTANEOUS EXCISIONAL BIOPSY DEVICE

BACKGROUND OF THE INVENTION

1. Field Of The Invention

The invention generally relates to medical devices, and more specifically to a device for excising breast lesions.

2. Description Of The Prior Art

Breast cancer has been and continues to be a most serious problem. Because the disease can be so devastating, more and more women seek to be tested for early signs of any abnormal growths in their breasts. One common procedure for such testing is mammography. However, this approach has disadvantages. If the mammogram showns any indication of a growth the typical next step is to take a needle biopsy and have it analyzed to determine if the growth is malignant. If it is the woman and her physician must make a decision as to whether to remove the growth using surgery or use another method of treatment. Of the approximately 400,000 breast biopsies taken in the United States every year about 90% are benign. However, for those cases where the growth is malignant, the woman may be required to return for surgery at a later date. This interim period is very stressful and filled with anxiety and fear. Also, surgery, particularly, radical mastectomies, can be traumatic and debilitating. Because such surgeries are major procedures, these require extensive hospital stays.

More recently, radiologists have used stereotactic breast biopsy machines for obtaining more accurate images of the abnormal growths. However, once found the same procedures were followed as with mammograms. The same is true with a laser scanning cytometer (LSC) developed by CompuCyte Corporation based in Cambridge, Mass., which appears to have the potential to advance the prognosis and management of breast-cancer patients. Unfortunately, when a malignant lesion has been removed and there is no lymph node involvement, traditional prognastic indicators such as tumor size and lymph node involvement are not accurate predictors of recurrence. Pathologists may need to look at cell cycle and cell proliferation analyses to identify which node-negative patients are at high risk for recurrence and therefore require close observation.

A number of surgical devices have been proposed for removing material from a patient without the use of conventional surgery. Compressible/expandable atherectomy cutters are disclosed in U.S. Pat. Nos. 4,966,604; 5.192,291; and 5,224,945. The prior art teaches flexible blades bent outwardly, the amount of expansion being controlled by a control element which can adjust the drive element through an infinite variety of positions while the blade rotates. A similar endovascular cutter for removing lesions constricting a vascular channel is disclosed in U.S. Pat. No. 5,318,576.

In U.S. Pat. No. 3,618,611 a vacuum rotary dissector is disclosed which is used for removing undesired tissue during surgery from difficult to reach locations. However, this dissector does not use compressible/expandable cutters.

SUMMARY OF THE INVENTION

It is an object of the invention to provide a surgical device which is particularly adapted to perform breast percutaneous excisional biopsies.

It is another object of the invention to provide a surgical device as in the last object which is simple in construction and inexpensive to manufacture.

It is still another object of the invention to provide a surgical device as in the previous objects which allows growths in a breast to be removed with minimal invasive surgery.

It is yet another object of the invention to provide a surgical device as aforementioned which can be effectively used to entirely remove a cancerous growth during stereotactic imaging.

It is a further object of the invention to provide a surgical device for excising abnormal breast tissue while minimizing clogging of the device as a result of clotting of blood which is removed with the biopsied and excised tissue.

In order to initially perform a biopsy of a tumor in a breast by excising it with minimaly invasive surgery a surgical device in accordance with the present invention comprises a support for facilitating the holding of the device. An elongate outer sleeve is mounted on said support and defines an axis and distal and proximate ends in relation to said support. An elongate inner tube is generally coaxial with and contained within said outer sleeve. Means are provided for selectively rotating said inner tube about said axis relative to said outer sleeve. Means are provided for selectively moving said outer sleeve along said axis relative to said inner tube between a first position is which the remote end of said inner tube in contained within and covered by said outer sleeve and a second position in which the remote end of said inner tube is exposed, said inner tube being provided at the remote end with a cutting assembly consisting of a plurality of blade elements radially spaced about said axis and biassed to urge said blade elements to expand outwardly into their normal operative cutting positions when moved exteriorly of said remote end of said outer sleeve, adjacent blade elements being collapsible for containment within said outer sleeve and forming laterally-directed opening which communicate with a channel within said inner tube. Means are provided for dispensing a carrier fluid F to said remote end of said outer sleeve. Means are provided for collecting tissue excised by said expanded blades carried through said inner tube from said remote to the proximate ends by the carrier fluid F. Also, means are provided for applying suction for extracting cells and tissue excised by said blade elements and transported by said carrier fluid F through said inner tube and into said means for collection.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts throughout.

DESCRIPTION OF THE PREFERRED EMBODIMENT

Figure 1:
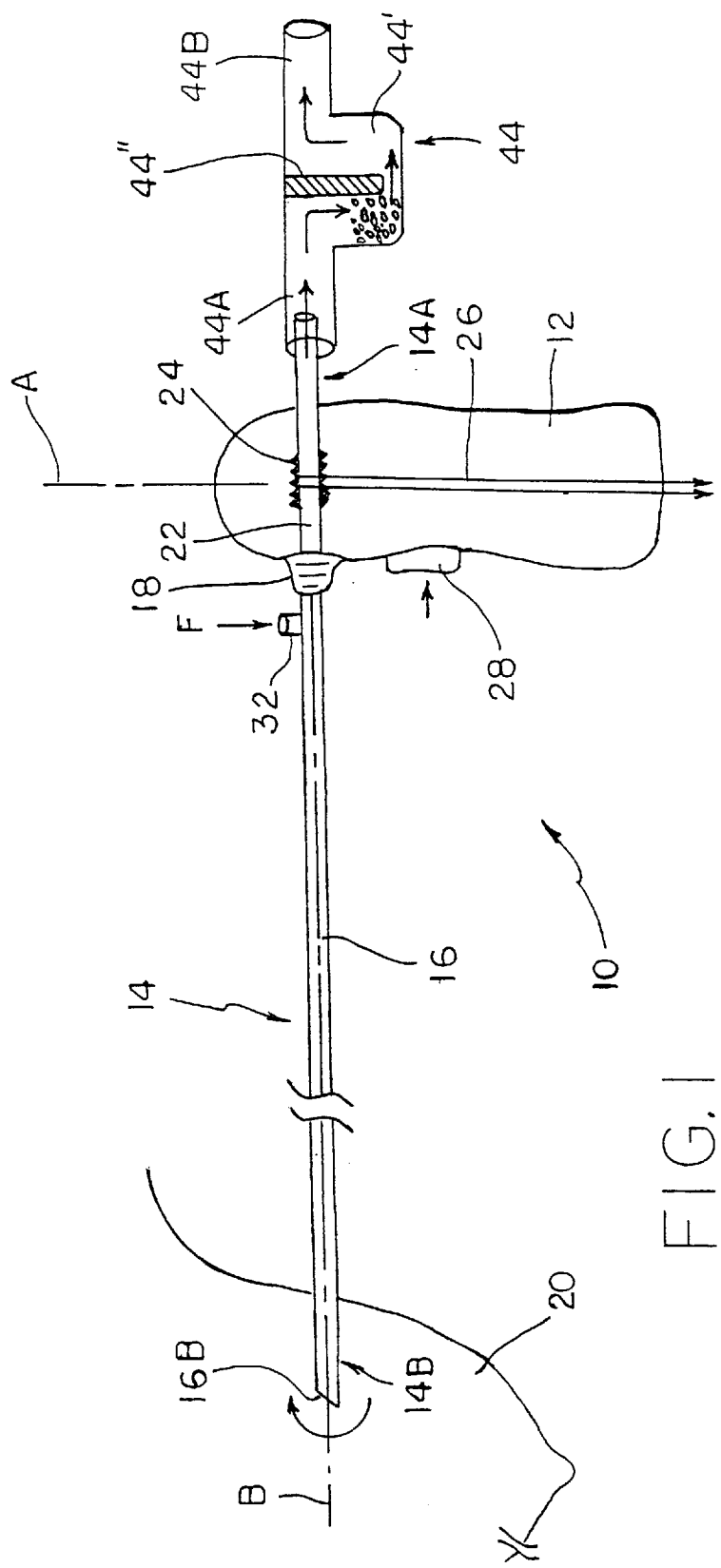
FIG. 1 is a schematic side elevational view of the surgical device in accordance with the invention, in partial cross-section, shown as used during a medical procedure to excise tissue from a human breast.

Referring to the drawings, and first referring to FIG. 1, the percutaneous excisional biopsy device in accordance with the invention is generally designated by the reference numeral 10.

The device 10 includes a support or handle 12 for facilitating the holding of the device by a user. Towards that end, the support 12 is preferably configured in the shape of a handgrip ergonomically designed to facilitate holding or gripping and may, for example, be in the general shape of a pistol grip, defining an axis A.

Figure 2:
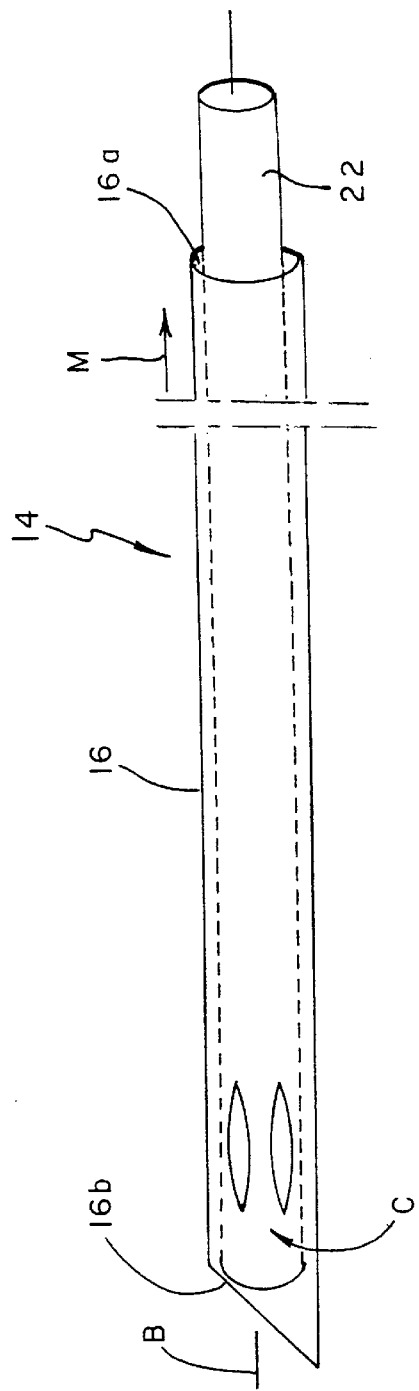
FIG. 2 is a schematic view of the probe portion of the device shown in FIG. 1, showing details of the cutting end of the inner tube when collapsed and contained within the outer sleeve.
Figure 3:
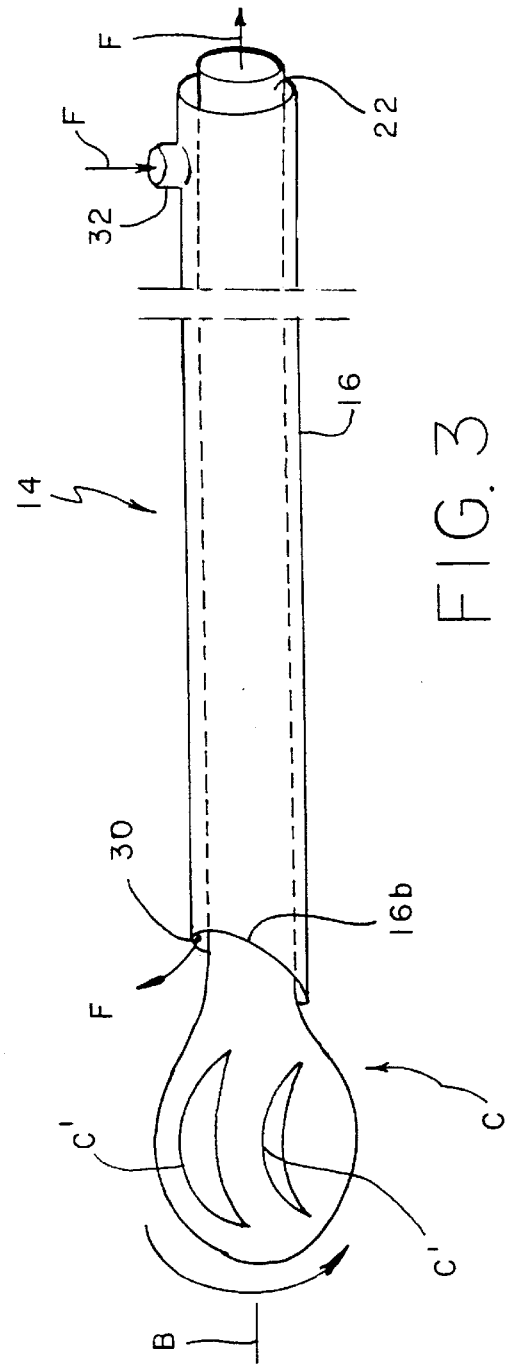
FIG. 3 is similar to FIG. 2 but showing the probe with the cutting end of the inner tube exposed beyond the remote end of the outer sleeve and expanded to the normal condition of the cutting elements.

Mounted on the handle 12 is a probe 14, which defines an axis B shown substantially normal to the axis A, and has a proximate end 14a at the handle 12 and a remote end 14b furthest from the handle 12. The probe 14 includes an outer sleeve 16 which is axially mounted on the handle 12 for slidable movement along the axis B. While any suitable mounting structure may be used, a flexible bellow 18 is illustrated for this purpose. The outer sleeve 16 has an interior cylindrical channel 16a and a tapered edge 16b at the free remote end 14b thereof as shown in FIGS. 1–3. The diameter of the outer sleeve 16 and the cutting edge 16b are selected to enable the remote end 14b to be introduced into the interior of a breast 20 through a skin incision of approximately 6–7 mm. Thus, the diameter of the outer sleeve 16 may be, for example, in the range of approximately 5–7 mm. Other suitable dimensions may be used as appropriate. The outer sleeve 16 may be formed of any suitable material. In the preferred embodiment, the outer sleeve is formed of any stable plastic such as PVC. Any other suitable plastic may be used which renders the outer sleeve 16 inexpensive and disposable.

An inner tube 22 is provided which is arranged within the channel 16a for movements in relation to the outer sleeve 16. The inner tube 22 is also preferably disposable and may be formed of any suitable spring steel or other strong material which may be formed with a cutting element C, to be more fully described in connection with FIGS. 4 and 5. One material presently preferred for the inner tube 22 is titanium because of its strength and light weight. The inner tube 22 is generally coaxial and co-extensive with the outer sleeve 16 on the probe portion 14 to the left of the handle 12, as viewed in FIG. 1. However, the inner tube 22 extends beyond the proximate end 14a of the probe 14 through the handle 12 as shown in FIG. 1. The dimensions of the inner tube 22 are selected to provide sufficient clearance within the channel 16a to permit relative axial sliding and rotation about axis B between the inner tube 22 and outer sleeve 16. The bellow 18 is used to urge or bias the outer sleeve 16 to the left relative to the handle 12, as viewed in FIG. 1, although any other biassing method, such as a compression spring, may be used to normally move the outer sleeve 16 to a position to cover the remote end of the inner tube 22 as shown in FIG. 2.

While the outer sleeve 16 is capable of limited axial movements along the axis B it is angularly fixed against rotation about said axis in any conventional way. However, the inner tube 22 is fixed against axial or linear movements along the axis B, although it is mounted for rotation about the axis B within the outer sleeve 16 which acts as a bearing. To selectively rotate the inner tube 22 any suitable drive may be used. By way of example only there is shown in FIG. 1 a profiled sheave or pulley 24 fixed to the inner tube 22, suitable drive cable 26 conventionally driven by a motor (not shown) is frictionally engaged or coupled to the pulley 24. An on-off switch 28 mounted on the handle 12 can be used to selectively activate the drive and rotate the pulley 24 and inner tube 22.

The clearance between the inner tube 22 and the outer sleeve 16 may also be used to carry and dispense a carrier fluid F at the remote end 14b of the probe 14. However, it will be clear that any other means for dispensing carrier fluid F at the remote end may be used, including a separate carrier channel or conduit 30 that extends along the probe 14. Alternately, a separate tube (not shown) may be used for this purpose. In FIGS. 1 and 3 a suitable vent or inlet port 32 is shown which may be used to feed carrier fluid F into the conduit 30 along the probe 14 to be dispensed in the region of the cutting edge 16b.

In FIG. 2 the outer sleeve 16 is shown in a first position relative to the inner tube 22 in which the inner tube 22 at the remote end is contained within and covered by the outer sleeve 16. In FIG. 3 the outer sleeve 16 is shown in a second position in which the inner tube at the remote end is exposed by movement of the outer sleeve 16 towards the right relative to the inner tube 22 (see arrow M in FIG. 2.) When in the first position, shown in FIG. 2, the outer sleeve 16 receives and covers the remote end of the inner tube which incorporates the cutting element C, to be described, leaving the tapered edge 16b at the remote end 14b of the outer sleeve 16 in a position suitable for guiding and penetrating the breast through an incision in the skin and soft tissues in the breast.

Figures 4, 5:
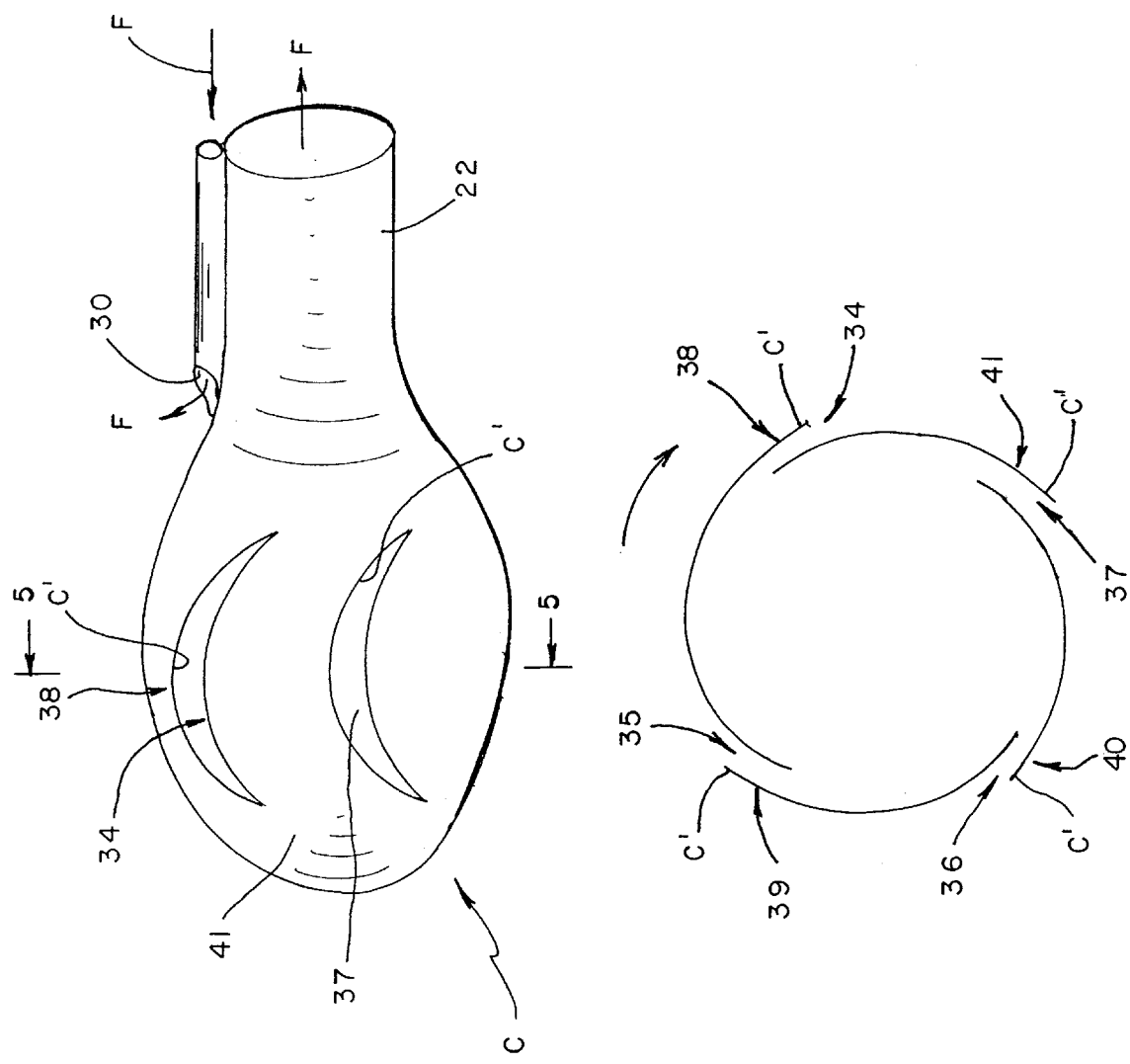
FIG. 4 is an enlarged view of the cutting elements in FIG. 3, showing the details of the cutting blades and the channel for dispensing carrier fluid F in the region where tissue is being removed.
FIG. 5 is a diagrammatic cross-section of the cutting elements of the inner tube taken along line 5—5 in FIG. 4.

Referring to FIGS. 4 and 5, the details are shown of one embodiment of a cutting element C at the remote end 14b of the inner tube 22, in which the remote end of the inner tube 22 is in the form of a sphere or an elliptical spheroid provided with a plurality of generally longitudinal slots or openings 34–37 circumferentially spaced from each other about the axis B of the inner tube. The slots 34–37 form an equal number of generally elongate cutting edges C' on cutting blades 38–41. When in the expanded condition shown in FIGS. 4 and 5 the cutting edges C' are positioned to cut soft tissues that come into contact with the cutting element C when the same rotates about its axis, in a clockwise direction as viewed in FIG. 5. However, it will be clear that the cutting element blades 38–41 can be arranged to provide the necessary cutting action when the cutter is rotated in the opposite direction.

The inner tube 22 is made from a relatively strong material, although sufficiently flexible and resilient to cause the cutting element C to naturally or normally expand from the retracted condition shown in FIG. 2 to the expanded condition shown in FIGS. 3–5 when permitted to do so. Preferably, the inner tube 22 is made from spring steel, although other materials, such as plastics, may be used as long as they can be formed with suitable cutting edges C'. In the embodiment shown, the outer sleave 16 can initiate and maintain the collapsed condition of the cutting element C by receiving the same within the internal channel 16a (FIG. 2). However, when the outer sleeve is moved relative to the inner tube 22 along the axis B to uncover the cutting element C the cutting blades 38–41 automatically expand or enlarge with rotation as the cutting edges C' cut the tissue and enlarge the cavity in the breast 20 within which the cutting element C is contained. While the inner tube 22 is mounted for rotation, as aforementioned, the external or outer sleeve 16 need not be mounted for rotation about the axis B but only for longitudinal sliding movements along that axis. In the embodiment described the outer sleeve 16 serves both the functions of guiding the probe 14 through the breast tissues to allow the cutting element C to be introduced into and to move the cutting blades 38–41 from one condition to another. However, it will be clear that these functions can also be achieved by using two separate and distinct elements, with different degrees of advantage.

An important feature of the invention is the use of a suitable fluid F for irrigating the tissues containing the cancerous or suspect cells, which fluid functions as a carrier for such cells from the excision site in the breast through the probe 14 into a receptacle 44 which has a collection chamber 44' with an inlet end 44$a$ connected to the probe 14 and an outlet end 44$b$ which can connected to a suitable source of vacuum or suction to draw the irrigation or carrier fluid F from the remote end 14$b$ through the collection chamber 44' and thereafter evacuated and suitably disposed of Inside the collection chamber 44' there is provided means for at least partially blocking or restricting the flow of the excised tissue or cells beyond the collection chamber 44' so that the same are collected therein for subsequent analysis. The specific blocking means used is not critical and may consist of a simple wall or partition 44" as shown, or may be in the form of a filter screen, a porous membrane or the like.

The operation of the surgical device will now be described. Referring to FIG. 1, the probe 14 is placed proximate to the region of the breast where the penetration is to take place. With the outer sleeve 16 in its fully extended position, to the left as viewed in FIG. 1, relative to the inner tube 22, the cutting element C is collapsed within the outer sleeve 16. Only the tapered edge 16$b$ is exposed to the tissue. After the tapered edge 16$b$ has penetrated through an incision in the outer and inner layers of tissue and has reached the site of the tissue desired to be analyzed the outer sleeve 16 is retracted, either manually or by the penetrated tissues, to expose the cutting blades 38–41, against the biasing action of a suitable spring or other resilient member, such as a rubber bellow 18. If the restoring force of the spring or the bellow 18 is sufficiently low it may allow movement of the outer sleeve 16 to the cutting blade exposed position in response to axial forces applied on the outer sleeve by the tissue being penetrated. Therefore, the outer sleeve 16 is retracted to expose the cutting element C when inside the breast and extended to cover the cutting element when withdrawn from the breast.

Once the cutting element C is placed proximate to the tissue to be analyzed, the switch 28 is depressed to actuate the drive and rotate the inner tube 22 and thereby the expanded cutting element C. The flow of the carrier fluid F may be commenced by the same switch 28 or by means of a separate control. The specific method of pumping the carrier fluid F is not critical and any known method may be used. Rotation of the inner tube 22 and the cutting element C causes the individual blades 38–41 to sweep against the tissue to be removed and to shave and sever the tissue to enable it to be transported from the breast 18 through the inner tube 22 to the receptacle 44 or collection chamber 44', where it is retained for further analysis. As indicated, the severed tissue and cells are transported by the irrigation/suction system and the continuous flow of saline solution or other carrier fluid F which prevents clogging and clotting in the tubes and enhances tissue transfer.

What has been described is a preferred embodiment of the invention, which is only given by way of example. Numerous modifications can be made to the disclosed embodiment without departing from the spirit of the invention. Thus, although an external or outer sleeve has been disclosed in connection with the preferred embodiment to initially collapse the cutting element C and enable the cutting element to expand to the cutting position when the sleeve is retracted, other mechanisms may be used to achieve this same or similar result. It is, therefore, the intention that the invention not be limited by the details of the preferred embodiment but only by the scope of the claims which are appended hereto.

We claim:

1. Surgical device for extracting cancerous or other tissue to be biopsied from a human breast, comprising a support for facilitating manual holding of the device; an elongate inner hollow tube defining an axis and having proximate and remote ends, said proximate end being rotatably mounted on said support and said remote end being dimensioned to be introduced through a small skin incision into the breast and advanced into close proximity to the region where the tissue sought to be excised is located; cutting means provided at said remote end of said elongate inner hollow tube, said cutting means including flexible cutting blades having cutting edges generally in the direction of said axis and formed to normally and naturally expand to expanded positions suitable for cutting adjacent tissue upon rotation of said elongate tube about said axis; an elongate outer hollow sleeve enclosing said inner hollow tube and mounted on said support for axial movements relative to said inner hollow tube for selectively engaging said cutting blades and forcing said blades to move to collapsed positions not suitable for cutting tissue and disengaging from said cutting blades to permit said blades to move to said normal and natural expanded position; drive means cooperating with said remote end of said inner hollow tube for selectively rotating said tube about said axis; means for irrigating a region containing the excised tissue with a carrier fluid; and collection means in fluid flow communication with said elongate inner hollow tube for collecting the excised tissue for analysis by receiving the carrier fluid after it has irrigated the region where said cutting means are positioned to excise tissue, whereby said outer hollow sleeve substantially covers and collapses said cutting blades when said remote end of said inner hollow tube and sleeve are introduced through an incision in the skin to advance said cutting blades to a location of the tissue to be removed and continues to protect adjacent tissue not to be removed during rotation of said inner hollow tube, and said blades can gradually and continuously expand after said outer hollow sleeve disengages from said cutting blades and an increasingly larger cavity is formed in the tissue to be removed as a result of the rotation and the cutting action of said cutting blades.

2. A surgical device as defined in claim 1, wherein said elongate inner hollow tube is made of a disposable plastic material.

3. A surgical device as defined in claim 1, wherein said support in the form of a handgrip.

4. A surgical device as defined in claim 3, wherein said handgrip is in the form of a pistol grip.

5. A surgical device as defined in claim 1, wherein said cutting means comprises longitudinal circumferentially spaced cutting blades.

6. A surgical device as defined in claim 5, wherein said cutting blades are formed of metal.

7. A surgical device as defined in claim 6, wherein said cutting blades are made of spring steel.

8. A surgical device as defined in claim 1, wherein said means for irrigating comprises conduit means for carrying the carrier fluid to the region where the tissue is to be excised and for moving the carrier fluid into said collection means.

9. A surgical device as defined in claim 8, wherein said irrigation means includes suction means for drawing the carrier fluid and excised tissue through said collection means.

10. A surgical device as defined in claim 1, further comprising biasing means for normally urging said outer hollow tube to move said cutting means to said collapsed condition against the inherent tendency of said cutting means to move to said expanded condition.

11. A surgical device as defined in claim 1, wherein said collection means includes a blocking member for blocking excised tissue when the carrier fluid passes therethrough.

12. A surgical device as defined in claim 11, wherein said blocking member comprises a partition or wall with small clearance sufficient for passage of carrier fluid but insufficient for passage of excised tissue.

13. A surgical device as defined in claim 11, wherein said blocking member comprises a filter.

14. A surgical device as defined in claim 11, wherein said blocking member comprises a permeable membrane.

15. A surgical device as defined in claim 1, wherein said cutting blades are elongate and generally extend along the direction of said axis.

* * * * *